United States Patent [19]

Myers

[11] Patent Number: 5,693,638
[45] Date of Patent: Dec. 2, 1997

[54] METHOD OF TREATING A MIGRAINE HEADACHE

[76] Inventor: Daniel Myers, 168 Thunderwood Dr., Bethel Park, Pa. 15102-1357

[21] Appl. No.: 802,748

[22] Filed: Feb. 20, 1997

Related U.S. Application Data

[60] Provisional application No. 60/012,192 Feb. 23, 1996.
[51] Int. Cl.$^6$ ................................................ A61K 31/54
[52] U.S. Cl. ........................................................ 514/224.8
[58] Field of Search ......................................... 514/224.8

[56] References Cited

PUBLICATIONS

Solomon Solis–Cohen, M.D. et al, "Pharmacotherapeutics Materia Medica and Drug Action" D. Appleton & Company, New York (1928) pps. 876–878.

*Primary Examiner*—Raymond J. Henley, III
*Attorney, Agent, or Firm*—Herbert Dubno; Jonathan Myers

[57] ABSTRACT

The present invention is directed to the treatment of a migraine headache with a composition containing leuko methylene blue as the active ingredient.

3 Claims, No Drawings

METHOD OF TREATING A MIGRAINE HEADACHE

CROSS REFERENCE TO RELATED APPLICATION

This application is related to Provisional Application Ser. No. 60/012,192 filed 23 Feb. 1996.

FIELD OF THE INVENTION

This invention relates to a method of treating a migraine headache. More particularly the invention relates to a method of treating a migraine headache employing the compound leuko methylene blue.

BACKGROUND OF THE INVENTION

A migraine headache may be defined as paroxysmal attacks of headache, frequently unilateral, usually accompanied by disordered vision and gastrointestinal disturbances. Vasodilation of extracerebral cranial arteries may be the cause of migraine headaches. See Taber's Cyclopedic Medical Dictionary, 16th Edition, Clayton L. Thomas, M.D. Ed., (F.A. Davis Company, Philadelphia 1989).

Pharmaceutical compositions that have been employed with some success in the treatment of migraine headaches include FIORINAL® and FIORICET® both products of SANDOZ. FIORINAL® contains aspirin, caffeine and butalbital whereas FIORICET® contains acetaminophen, caffeine and butalbital. Both of these drugs may also include codeine. Butalbital and codeine are both habit-forming and potentially abusable. Side effects of both FIORINAL® and FIORICET® include drowsiness and oftentimes patients taking these medications still do not obtain adequate relief from the headaches.

There is disclosure in the prior art for the use of methylene blue to treat a migraine headache. See *Pharmacotherapeutics Material Medica and Drug Action*, Solomon Solis-Cohen, M.D. et al, pp 876 to 878 (D. Appleton & Co., New York 1928). On page 878 of the reference it is indicated that some success in the treatment of migraine and nervous headache has been observed employing methylene blue. No indication of employing leuko methylene blue in the treatment of migraine headache is found in the reference although the reference does note that leuko methylene blue, a reduced form of methylene blue does exist.

OBJECT OF THE INVENTION

It is the object of the invention to provide a new, highly effective treatment for migraine headache.

SUMMARY OF THE INVENTION

I have found that the administration of leuko methylene blue to a patient in need of treatment of migraine headache brings about a surprisingly high level of pain relief. Leuko methylene blue, which is a reduced form of methylene blue, has the following structural formula:

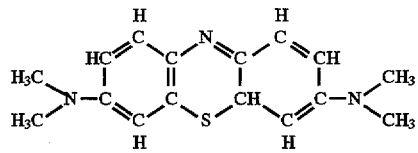

While any route of administration of the leuko methylene blue is contemplated to be within the scope of the invention, the preferred routes of administration include the sublingual and transdermal methods of administration. The sublineal route of administration employs a tablet or dragee that is placed underneath the tongue where absorption of the drug through the mucous membranes of the mouth takes place. In the case of transdermal administration the compound is provided in the form of an ointment or cream that may be rubbed into the skin or in a reservoir in a transdermal patch that may be attached for example to the arm or leg of the patient.

The pharmaceutical composition containing the leuko methylene blue may preferably be in a sustained-release form in order to permit a controlled level of the leuko methylene blue in the bloodstream over an extended period of time.

The preferred dosage range for the leuko methylene blue is 0.1 to 20 mg/kg of body weight of the patient. The preferred daily dosage ranges from 65 to 260 mg/day. Preferably the dosage is divided up to provide three or four daily doses.

Processes to prepare the leuko methylene blue by reduction of methylene blue are well known in the art. According to Baker, T. R. *Principles of Biological Microtechnique: A Study of Fixation and Dyeing*, Methuen, London (1958), reduction of methylene blue using sodium thiosulfite and acid may be carried out. Or the addition of sodium sulphoxylate with formaldehyde may reduce the methylene blue to leuko methylene blue. According to Gurr, E., *Synthetic Dyes in Biology, Medicine and Chemistry*, Academic Press, London (1971) reduction may be carried out of the methylene blue in dilute sulfuric acid with zinc dust. According to Venkataraman, Chemistry of Synthetic Dyes, Vol. 2, Academic Press, New York (1952), reduction may take place using ferrous sulfate and irradiation. And according to Bongard et al in 1995, the reduction may take place in vitro by cultured bovine artery epithelial cells.

The leuko methylene blue can be formulated into pharmaceutical compositions by known methods of the pharmaceutical industry. The active ingredient can be finished in conventional dosage forms (e.g. tablets, pills, coated pills, dragees, capsules, injections, or in the form of the transdermal patch. The pharmaceutical compositions can comprise the usual carriers, additives, fillers, auxiliary agents, etc.

In the following examples the preparation of pharmaceutical compositions comprising leuko methylene blue as active ingredient is described.

EXAMPLE 1

Dragees (coated pills) having the following composition are prepared:

| Component | Amount mg/dragee core |
| --- | --- |
| Leuko methylene blue | 30 |
| Maize starch | 51 |
| Lactose | 82 |
| Luviscol VA64 | 4 |
| Stearin | 4 |
| Avicel | 25 |
| Talc | 4 |
| Total weight | 200 |

The dragee core is prepared as follows:

The leuko methylene blue, the maize starch and the lactose are homogenized (Mixture I). The Luviscol and stearin are dissolved in isopropanol (Solution II).

The homogeneous powder Mixture (I) is granulated with the isopropanol solution (II). The granules are dried and regranulated on a sieve no. 16. The Avicel and talc are added and homogenized. Dragee cores are prepared by using a convex die having a diameter of 10 mm. The dragee core thus obtained can be coated with a syrup or film layer by conventional methods: (e.g. H. A. Lieberman, L. Lachmann: Pharmaceutical dosage forms, Marcel Dekkar Inc. New York 1982.

EXAMPLE 2

Tablets having the following composition are prepared:

| Component | Amount mg/tablet |
| --- | --- |
| Leuko methylene blue | 30 |
| Maize starch | 29 |
| Lactose | 24 |
| Maize starch | 9 |
| Gelatin Alba | 3 |
| Talc | 3 |
| Magnesium stearate | 2 |
| Total weight | 100 |

The tablets are prepared as follows:

The leuko methylene blue, maize starch and lactose are sieved and homogenized, whereupon the mixture is granulated with an about 5% aqueous gelatine solution. The granules are dried to a moisture content of 2% and re-granulated on a sieve No. 18. To the granules as external phase the remaining part of maize starch, talc and magnesium stearate are added and from the mixture tablets are pressed by using a die having a diameter of 8 mm.

EXAMPLE 3

A suitable mixture for transdermal treatment according to the invention consists of 3 parts of leuko methylene blue mixed with 97 parts of an ointment base. The composition of the ointment base is as follows:

| | |
| --- | --- |
| Polyethylene glycol 6000 distearate | 5 to 15% |
| Polyethylene glycol 1540 | 15 to 25% |
| Butylated hydroxytoluene preservative | 0.1 to 1.0% |
| Polyethylene glycol 300 | balance |

An amount of 0.5 to 2.0 g of this medicated ointment is applied to the forearm of a patient suffering from a migraine headache and rubbed into the skin to provide a therapeutically effective amount of leuko methylene blue for at least one day.

EXAMPLE 4

This is an example of a transdermal patch incorporating leuko methylene blue. Five to fifty mg of this drug are dissolved in a mixture of mineral oil and polyisobutylene to provide a liquid center reservoir of active drug. This reservoir is enclosed in a sealed, flat, disk-shaped pouch, one to six cm in diameter. The top of the pouch consists of a thin aluminized polyester film that is impermeable to the pouch contents. The bottom of the pouch that will be in contact with the skin in use consists of a thin polypropylene membrane that is slowly porous to leuko methylene blue, allowing the drug to continuously come into contact with the skin, so long as the bottom of the pouch is in contact with the skin. The bottom of the pouch also includes a thin coat of a hypoallergenic silicone adhesive disposed on the bottom in such a way as to hold the patch firmly to the skin without unduly impeding the permeation of the drug through the membrane. As manufactured, a protective strip of siliconized polyester film covers the polypropylene membrane. This siliconized film is impermeable to the liquid mixture and thus protects the pouch's therapeutic contents during storage. The protective film is removed by the patient prior to the attachment of the pouch to the skin.

What is claimed is:

1. A method of treating a migraine headache in a patient in need of said treatment which comprises the step of administering to said mammalian subject, a therapeutically effective amount of leuko methylene blue.

2. The method of treating a migraine headache defined in claim 1 wherein the leuko methylene blue is administered sublingually.

3. The method of treating a migraine headache defined in claim 1 wherein the leuko methylene blue is administered transdermally.

* * * * *